US010484614B2

(12) United States Patent
Kim

(10) Patent No.: US 10,484,614 B2
(45) Date of Patent: Nov. 19, 2019

(54) APPARATUS FOR OBSERVING FINE OBJECT

(71) Applicant: Korea Research Institute of Chemical Technology, Daejeon (KR)

(72) Inventor: Woo-Keun Kim, Daejeon (KR)

(73) Assignee: KOREA RESEARCH INSTITUTE OF CHEMICAL TECHNOLOGY, Daejeon (KR)

(*) Notice: Subject to any disclaimer, the term of this patent is extended or adjusted under 35 U.S.C. 154(b) by 170 days.

(21) Appl. No.: 15/623,131

(22) Filed: Jun. 14, 2017

(65) Prior Publication Data

US 2018/0097999 A1 Apr. 5, 2018

(30) Foreign Application Priority Data

Jun. 14, 2016 (KR) ........................ 10-2016-0074075
Jan. 20, 2017 (KR) ........................ 10-2017-0009744

(51) Int. Cl.

| | |
|---|---|
| ***H04N 17/00*** | (2006.01) |
| ***H04N 5/225*** | (2006.01) |
| ***H04N 5/232*** | (2006.01) |
| ***G01N 21/84*** | (2006.01) |
| ***G01N 33/483*** | (2006.01) |
| ***H04N 7/18*** | (2006.01) |

(52) U.S. Cl.

CPC ......... *H04N 5/23296* (2013.01); *G01N 21/84* (2013.01); *G01N 33/4833* (2013.01); *H04N 5/2256* (2013.01); *H04N 5/23293* (2013.01); *H04N 7/185* (2013.01); *H04N 7/181* (2013.01)

(58) Field of Classification Search

CPC ... G01N 21/84; G01N 33/4833; H04N 5/2256
USPC ................................ 348/142, 143, 169, 135
See application file for complete search history.

(56) References Cited

U.S. PATENT DOCUMENTS

2017/0289416 A1* 10/2017 Umemura ............ G01B 11/002

FOREIGN PATENT DOCUMENTS

| | | |
|---|---|---|
| JP | 2003195174 A | 7/2003 |
| JP | 2011048013 A | 3/2011 |
| JP | 2011109644 A | 6/2011 |
| JP | 2013054083 A | 3/2013 |
| JP | 2013145318 A | 7/2013 |
| JP | 2014186332 A | 10/2014 |
| JP | 2014194376 A | 10/2014 |
| JP | 2014219623 A | 11/2014 |

(Continued)

*Primary Examiner* — Jefferey F Harold
*Assistant Examiner* — Jean W Desir
(74) *Attorney, Agent, or Firm* — Perkins Coie LLP

(57) ABSTRACT

An apparatus for observing a fine object is disclosed. The observation apparatus includes: a camera configured to capture each of a plurality of fine objects contained in at least some of a plurality of partitioned wells of a plate; a drive unit configured to allow the camera to relatively move with respect to the plate in such a manner that the camera scans the plate; and a controller configured to control the drive unit in such a manner that the camera captures only at least some wells having the plurality of fine objects from among the plurality of wells. The controller determines a shortest movement route of the camera on the basis of a position of at least some wells having the plurality of fine objects, and controls the drive unit in such a manner that the camera moves in the determined shortest movement route.

18 Claims, 15 Drawing Sheets

(56) References Cited

FOREIGN PATENT DOCUMENTS

| | | | |
|---|---|---|---|
| JP | 2015007801 | A | 1/2015 |
| KR | 1020130055932 | A | 5/2013 |

* cited by examiner

APPARATUS FOR OBSERVING FINE OBJECT

CROSS-REFERENCE TO RELATED APPLICATION

This application claims priorities to and benefits of Korean Patent Application No. 10-2016-0074075 filed on Jun. 14, 2016 and Korean Patent Application No. 10-2017-0009744 filed on Jan. 20, 2017. The entire contents of the aforementioned patent application are incorporated by reference as part of the disclosure of this patent document.

TECHNICAL FIELD

The present disclosure relates to an apparatus for observing a fine object.

BACKGROUND

Recently, fish eggs, especially, zebra fish eggs, have been widely used as laboratory animals that replace rodents for studies on acute toxicity and developmental toxicity. Different experimental conditions are set in respective wells of a multiwell plate to hatch eggs, and a heart rate of a differentiation and development process is observed, such that harmfulness of each harmful substance is assessed.

SUMMARY

This patent document provides implementations and examples of an apparatus for observing a fine object. The examples for implementing the apparatus include observing fish eggs (i.e., roe or spawn of fish) and developmental toxicity of fish. Some implementation of the disclosed technology provide an apparatus for evaluating harmful substances affecting fish eggs and development thereof. The disclosed technology allows to measure fine objects in more accurate and faster manner.

In one aspect, an apparatus for observing a fine object includes: a camera configured to capture each of a plurality of fine objects contained in at least some of a plurality of partitioned wells of a plate; a drive unit configured to allow the camera to relatively move with respect to the plate in such a manner that the camera scans the plate; and a controller configured to control the drive unit in such a manner that the camera captures only at least some wells having the plurality of fine objects from among the plurality of wells, wherein the controller determines a shortest movement route of the camera on the basis of a position of at least some wells having the plurality of fine objects, and controls the drive unit in such a manner that the camera moves in the determined shortest movement route.

The controller may determine the position of at least some wells having the fine objects from among the plurality of wells according to a predetermined method.

The predetermined method may be a method for determining a position of each well having the fine object on the basis of a specific position at which an image satisfying a predetermined condition is detected in an overall image acquired when the entirety of the plurality of wells is captured once.

The apparatus may further include: a display unit configured to output an image captured by the camera, wherein the image is at least one of a still image (stopped image) and a moving image (video image).

A plurality of images corresponding to the respective wells may be output and displayed on the display unit; and the controller may change the shortest movement route on the basis of the positions of wells corresponding to user-selected images from among the plurality of images.

The controller may control the drive unit in a manner that the camera sequentially performs first movement and second movement, wherein the first movement indicates that the camera moves along the shortest movement route at one side of the plate, and the second movement indicates that the camera moves along the shortest movement route at the other side of the plate.

The camera may rotate about the fine object by the drive unit in such a manner that the camera captures an upper part of the fine object and a lower part of the fine object when located at one side and the other side of the plate.

The controller may control the drive unit in such a manner that the camera repeatedly performs a single set of the first movement and the second movement according to the number of iterations entered by a user.

The controller may control the drive unit in such a manner that the camera performs the single set of movements and then performs a next set of movements according to a time interval value entered by the user.

When the camera captures each of at least some wells having the plurality of fine objects, the camera may capture each well at a first magnification and may then capture the well at a second magnification higher than the first magnification.

The controller may determine a specific part corresponding to a portion satisfying a predetermined condition within an image captured at the first magnification, to be a detailed position of the fine object. When the camera performs image capture at the second magnification, the controller may control the drive unit in a manner that the position of the camera is adjusted on the basis of the determined detailed position of the fine object.

A fine-object image magnified at the second magnification may be located at the center of the captured image.

The drive unit may control the camera to move in a single direction parallel to one surface of the plate having the fine object.

The single direction may be at least one of first and second directions orthogonal to each other and a third direction denoted by a combination of the first direction and the second direction.

If the fine object is a fish egg, at least one of a movement speed of the camera and an image capture time for each well may be determined on the basis of a differentiation time of the fish egg and the determined shortest movement route in such a manner that the scanning is completed within the differentiation time of the fish egg.

If the fine object is a fish egg, at least one of a movement speed of the camera and an image capture time for each well may be determined on the basis of a differentiation time of the fish egg, the determined shortest movement route, and the number of iterations entered by the user in such a manner that camera movement is repeatedly performed according to the user-input iteration number received within the differentiation time of the fish egg.

If the fine object is a fish egg, at least one of a movement speed of the camera and an image capture time for each well may be determined on the basis of a differentiation time of the fish egg, the determined shortest movement route, and the number of iterations entered by the user in such a manner that camera movement is repeatedly performed according to the user-input iteration number received within the differentiation time of the fish egg.

The apparatus may further include a backlight unit configured to face the camera, and emit light to the fine object.

The camera and the backlight unit may be integrated into a frame in such a manner that the camera rotates along with the backlight unit.

Those and other features are described in greater detail in the drawings, the description and the claims.

DETAILED DESCRIPTION OF THE EMBODIMENTS

Figure 1:
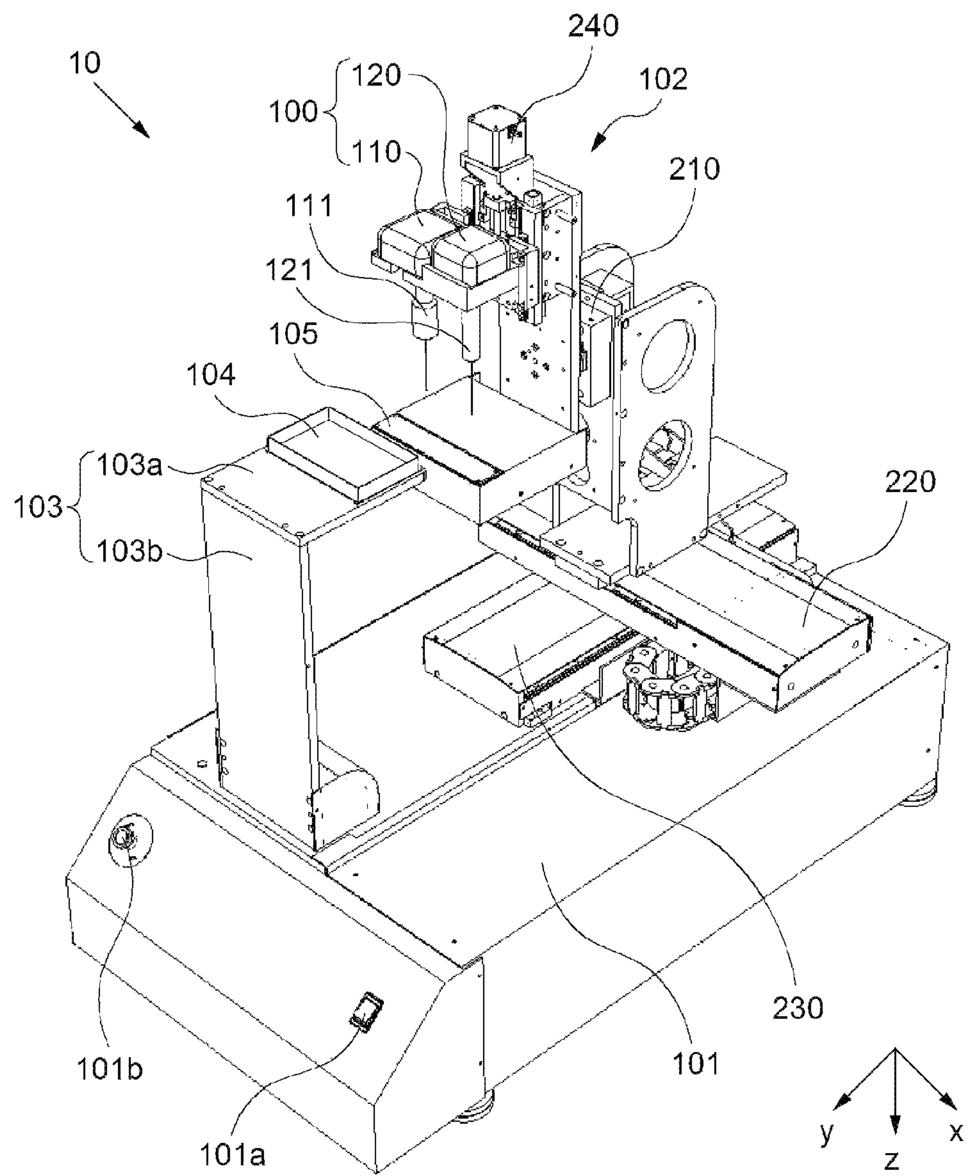
FIG. 1 is a perspective view illustrating an exemplary apparatus for observing a fine object according to one implementation of the present disclosure.

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the other element or intervening elements may also be present. In contrast, when an element is referred to as being "directly connected with" another element, there are no intervening elements present.

A singular representation may include a plural representation unless otherwise stated in the context.

In the present application, the terms "including" or "having" are used to indicate that features, numbers, steps, operations, components, parts or combinations thereof described in the present specification are present and presence or addition of one or more other features, numbers, steps, operations, components, parts or combinations is not excluded.

In observing a fine object, a multiwall plate is used for setting different experimental conditions. The multiwell plate is a transparent tool configured to contain an observation object, and include multiple wells that are arranged in rows and columns within a plane. Different experimental conditions may include different harmful substances. Since a differentiation time of fish eggs is very fast as about 3 to 4 hours, there is a need to finish experimentation and observation within a short period of time. In association with toxicity in the developmental process, the developmental toxicity can be recognized using the beats per minute. To have the developmental toxicity using the beats per minute, a heart rate is obtained by observing heart beats for one or more minutes, and the heart rate is converted into a beats per minute. When observing developmental toxicity, however, the following problems may occur.

First, due to unnecessary time consumption caused by a manual operation and a difference between observation viewpoints of wells, it is difficult to observe wells of a plurality of multiwell plates within a given differentiation time. The manual operation may refer to a series of processes including a process for designating the position of each well, a process for setting a focal point, and a process for capturing images of a current well and moving to the next well.

Second, a user who uses a microscope may observe only an object located below the microscope. In contrast, eggs sink to the bottom of the well, such that top-view imaging of objects placed in the well may be easier and clearer than bottom-view imaging of objects placed in the well. Thus, experimental efficiency is deteriorated. The number of samples capable of being simultaneously contained in the multiwell plate may be limited to a given number of samples capable of being completely tested within a differentiation time. Specifically, a long observation time is consumed to measure the heart rate using the microscope, such that the accuracy of the test result may be reduced and it is possible to perform a large number of tests.

In addition, since ultrasonic waves are not reflected from fish eggs and are absorbed into the fish eggs, an ultrasonic imaging apparatus may be inappropriate for observing fish eggs.

In recognition of the problems above, the disclosed technology provides various implementation of an apparatus for observing a fine object that can obviate and solve the problems above and observes the fine object in an accurate way.

Figure 2A:
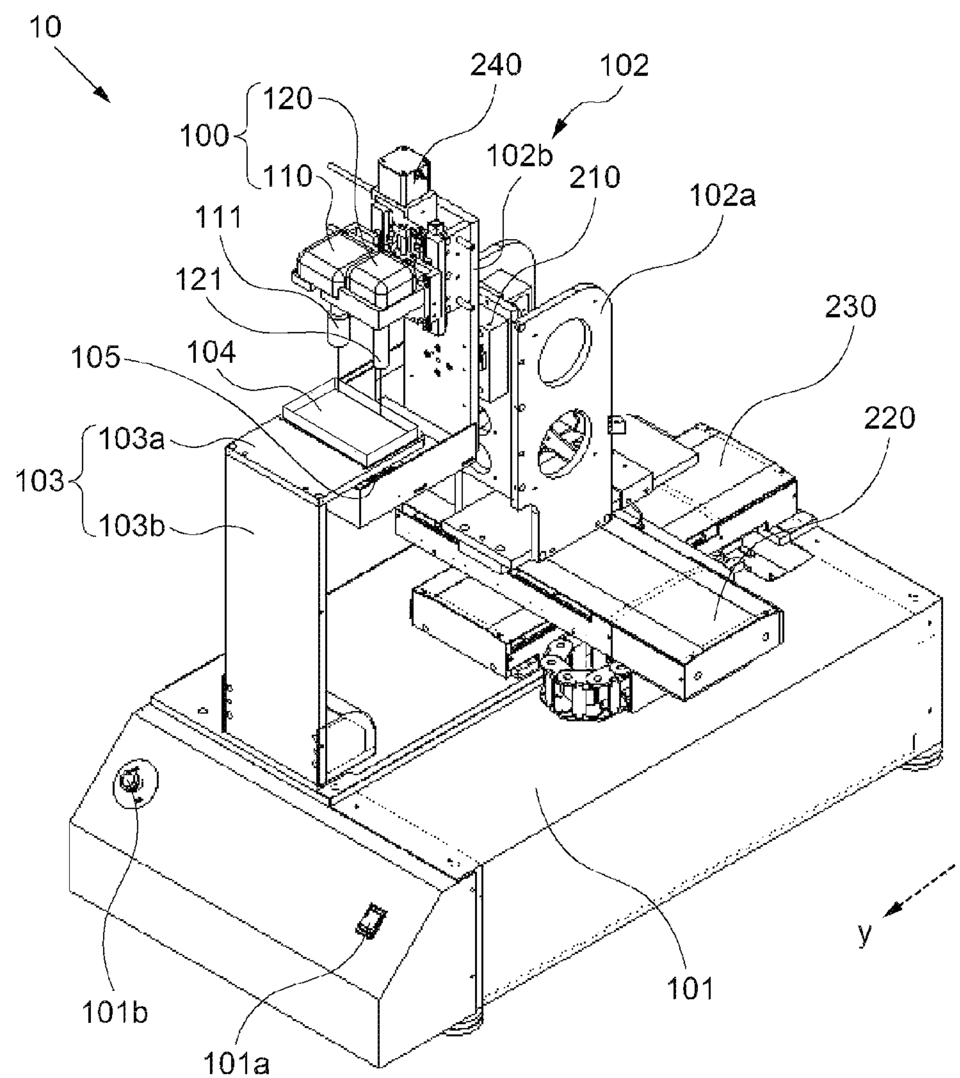
FIGS. 2A and 2B illustrate operations of a drive unit related to R-axis directional movement of an exemplary apparatus for observing a fine object according to one implementation of the present disclosure.
Figure 2B:
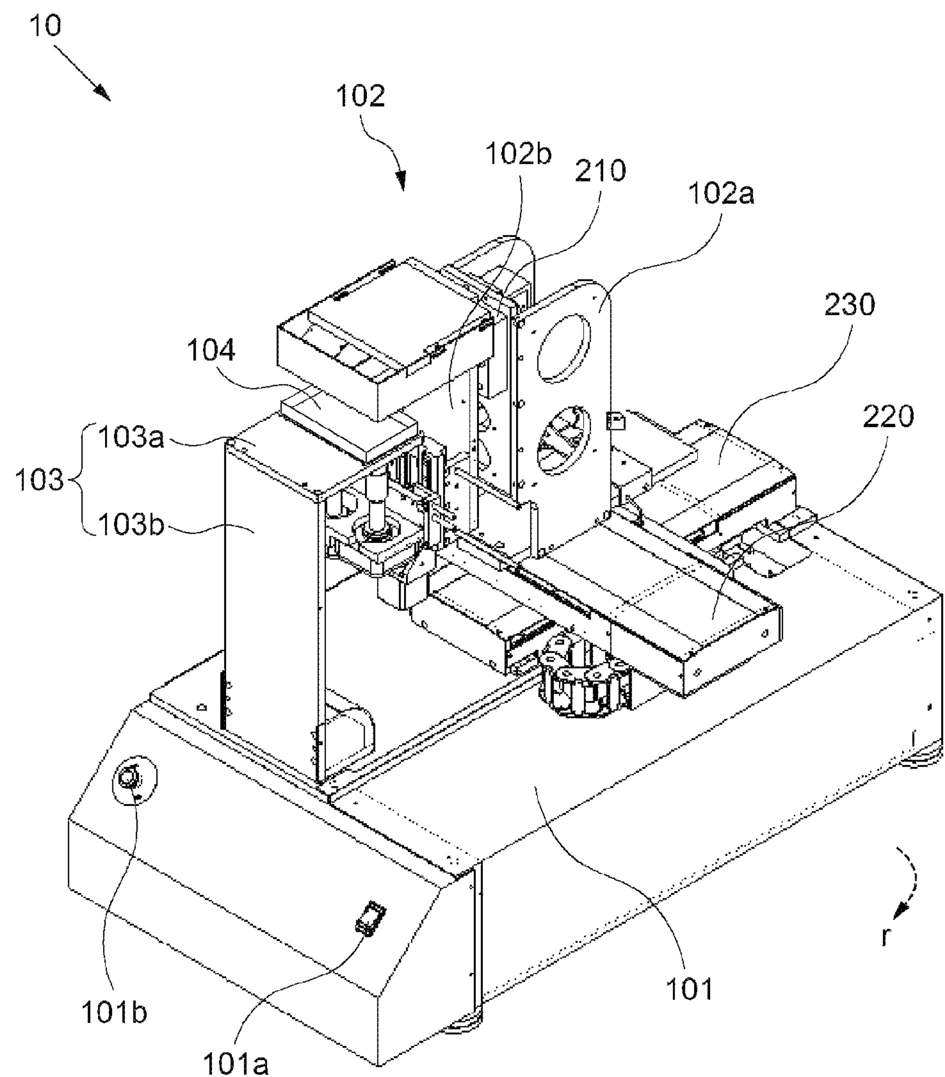

FIG. 1 is a perspective view illustrating an exemplary apparatus 1 for observing a fine object according to an embodiment of the present disclosure. FIGS. 2A and 2B illustrate exemplary views in which an apparatus for observing a fine object is being operated according to an embodiment of the present disclosure.

The observation apparatus 1 according to the present disclosure may include a camera 100, a drive unit 200, and a control unit 300.

The camera 100 according to the present disclosure may include first and second lenses (111, 121) configured to acquire images of a fine object using at least one of a first magnification and a second magnification.

For example, the first lens 111 may be a low-magnification lens, and the second lens 121 may be a high-magnification lens. In more detail, the first lens 111 may have a range magnification of a magnification of 0.7× to 2.0×, and the second lens 121 may have a range magnification of 10× to 50×.

Alternatively, the camera 100 according to the present disclosure may include a first camera 110 and a second camera 120. The first and second cameras 110 and 120 may be configured to capture images having different magnifications. The first camera 110 and the second camera 120 may be arranged parallel to each other.

In this case, the first lens 111 and the second lens 121 may be contained in the first camera 110 and the second camera 120, respectively.

The camera 110 according to the present disclosure may further include various constituent elements needed for camera operations and capture of images (e.g., still images or moving images), for example, a filter, an image sensor, etc.

Meanwhile, the apparatus for observing a fine object according to the present disclosure may include a main body 101 and a frame 102 movable with respect to the main body 101. The main body 101 and the frame 102 may form overall appearance of the observation apparatus for a fine object.

The main body 101 may support the frame 102, and may be placed on the ground. In addition, the main body 101 may include a switch 101*a* and an EMO switch 101*b* to control on or off operations of the observation apparatus 10.

A test table 103 on which a plate 104 is placed may be located at one side of the main body 101. In this case, the test plate 103 may include a first test plate 103*a* and a second test plate 103*b*. The first test plate 103*a* and the second test plate 103*b* may be arranged perpendicular to each other. The first test plate 103*a* may be arranged approximately parallel to the main body 101. The second test plate 103*b* may connect the first test plate 103*a* to the second test plate 103*b*.

At the other side of the main body 101, the frame 103 may be movably connected to the main body 101. Meanwhile, the frame 102 may include a first frame 102*a* and a second frame 102*b*. A detailed description thereof will hereinafter be given with reference to FIG. 2A.

The drive unit 200 may be configured to move at least one of the frame 102 and the camera 100 with respect to the main body 101.

In more detail, the drive unit 200 may include first to fourth drive units 210, 220, 230, and 240. Each of the first to fourth drive units 210, 220, 230, and 240 may move at least one of the frame 102 and the camera 100 of the observation apparatus 1 in the directions of R-X-Y axes and the Z-axis.

The first drive unit 210 may move the camera 100 in a manner that the camera 100 can capture images of the fine object in a plurality of directions.

In more detail, the first drive unit 210 may rotate the camera 100 such that the camera 100 can capture a top or bottom view of the fine object. That is, the camera 100 may rotate about the fine object by the first drive unit 210.

FIG. 2A illustrates an exemplary case in which the camera 100 is arranged at an upper part of the fine object, and FIG. 2B illustrates an exemplary case in which the camera 100 is arranged at a lower part of the fine object.

Meanwhile, as described above, the frame 102 according to the present disclosure may include a first frame 102*a* and a second frame 102*b*. In this case, the camera 100 may be fixed to the second frame 102*b*, and the first and second frames 102*a* and 102*b* may be rotatably connected to each other by the first drive unit 210.

Referring to FIGS. 2A and 2B, since the second frame 102*b* rotates about the first frame 102, the camera 100 mounted to the second frame 102*b* may rotate about the fine object.

By the above-mentioned structure, various aspects of the fine object are captured by the camera 100 such that the user can more closely observe the fine object. In addition, the heart rate of eggs placed at the bottom of the plate can be easily measured. In this case, the plate 104 containing the fine objects may be comprised of a light transmission material.

In the meantime, the camera 100 may be arranged above or below fine objects, and may also be arranged at other parts of the fine objects. In other words, one case, in which the camera 100 is arranged above the fine objects may indicate that the position of the camera 100 corresponds to 0°, and the other case, in which the camera 100 is arranged below the fine objects may indicate that the position of the camera 100 corresponds to 180°, the camera 100 may also be located at any one of 0° to 180°.

In addition, when the camera 100 is located at any one of the upper part and the lower part of fine objects and is then located at the other one, the camera 100 may rotate clockwise or counterclockwise.

The second drive unit 220 may move the frame 102 in an X-axis direction. If the frame 102 moves in the X-axis direction, the camera 100 fixed to the frame 102 may also move in the X-axis direction. According to such movement of the camera 100, the camera 100 may scan the fine objects in the X-axis direction even when the fine objects are placed on the test table throughout a wide region.

In more detail, the second drive unit 220 may include a stepper motor, a linear motion (LM) guide, a ball screw, a coupling, a limit sensor, and a home sensor.

Figure 3A:
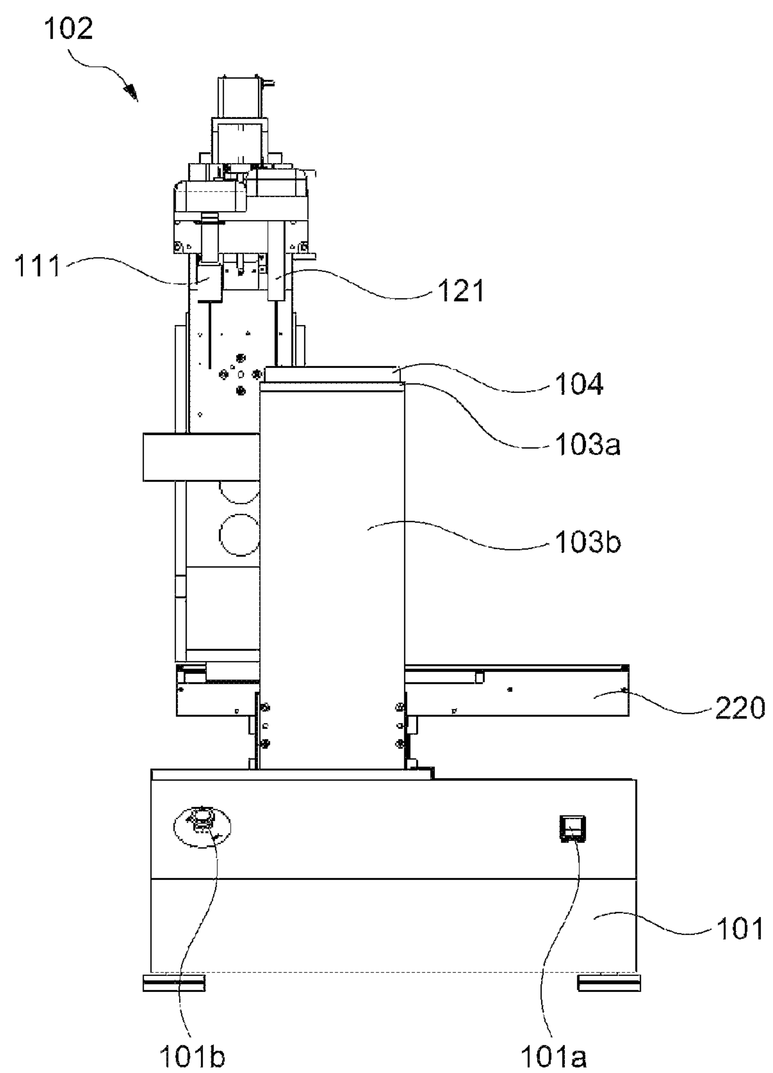
FIGS. 3A and 3B illustrate operations of a drive unit related to X-axis directional movement of a frame according to one implementation of the present disclosure.
Figure 3B:
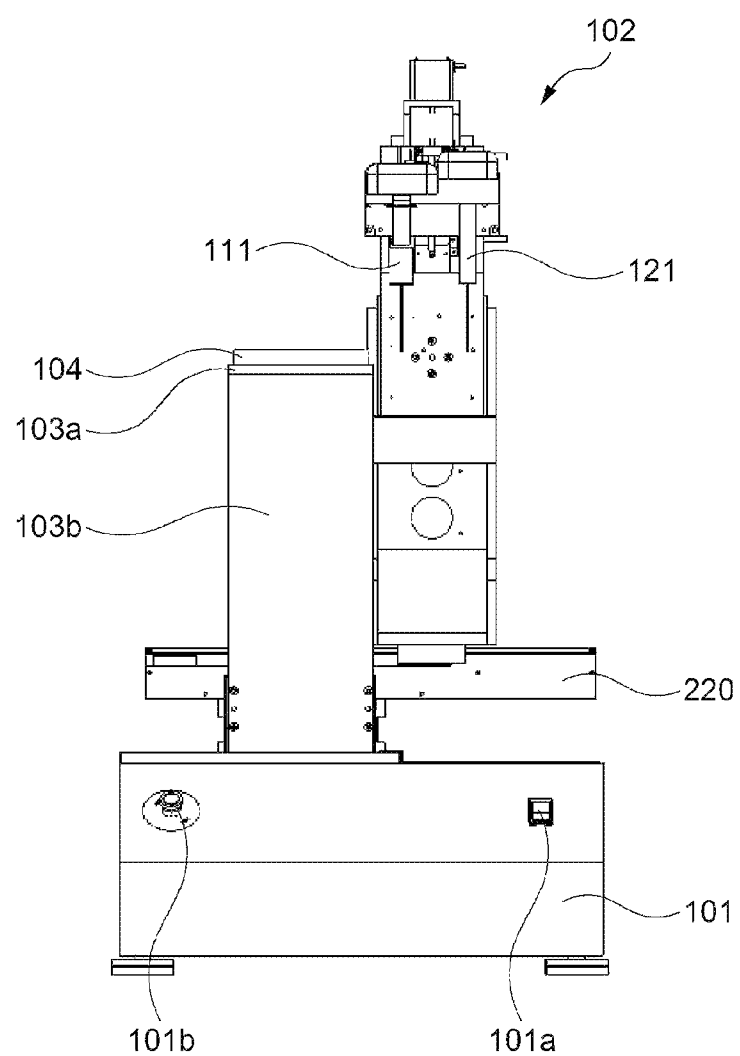

Referring to FIG. 3, a moving stroke of the second drive unit may be about 210 mm. In addition, the distance between two limit sensors (i.e., one pair of limit sensors) located at both sides of the LM guide may be about 200 mm. In addition, a ball screw lead may have a size of about 2 mm. Meanwhile, the above-mentioned numerical values are merely examples, and the present disclosure is not limited thereto.

The third drive unit 230 may move the frame 102 in the Y-axis direction. If the frame 102 moves in a Y-axis direction, the camera 100 fixed to the frame 102 may also move in the Y-axis direction. By such movement, even when fine objects are placed on the test table throughout a wide region, the fine objects may be scanned in the Y-axis direction.

In more detail, detailed constituent elements of the third drive unit 230 may be identical to those of the second drive unit 220. In addition, the LM guide of the second drive unit 220 may be arranged approximately perpendicular to the LM guide of the third drive unit 230.

In this case, the LM guide of the second drive unit 220 may linearly move in the LM guide of the third drive unit 230, and the frame may be fixed to the second drive unit 220, such that the frame 102 may be moved in the Y-axis direction.

Figure 4A:
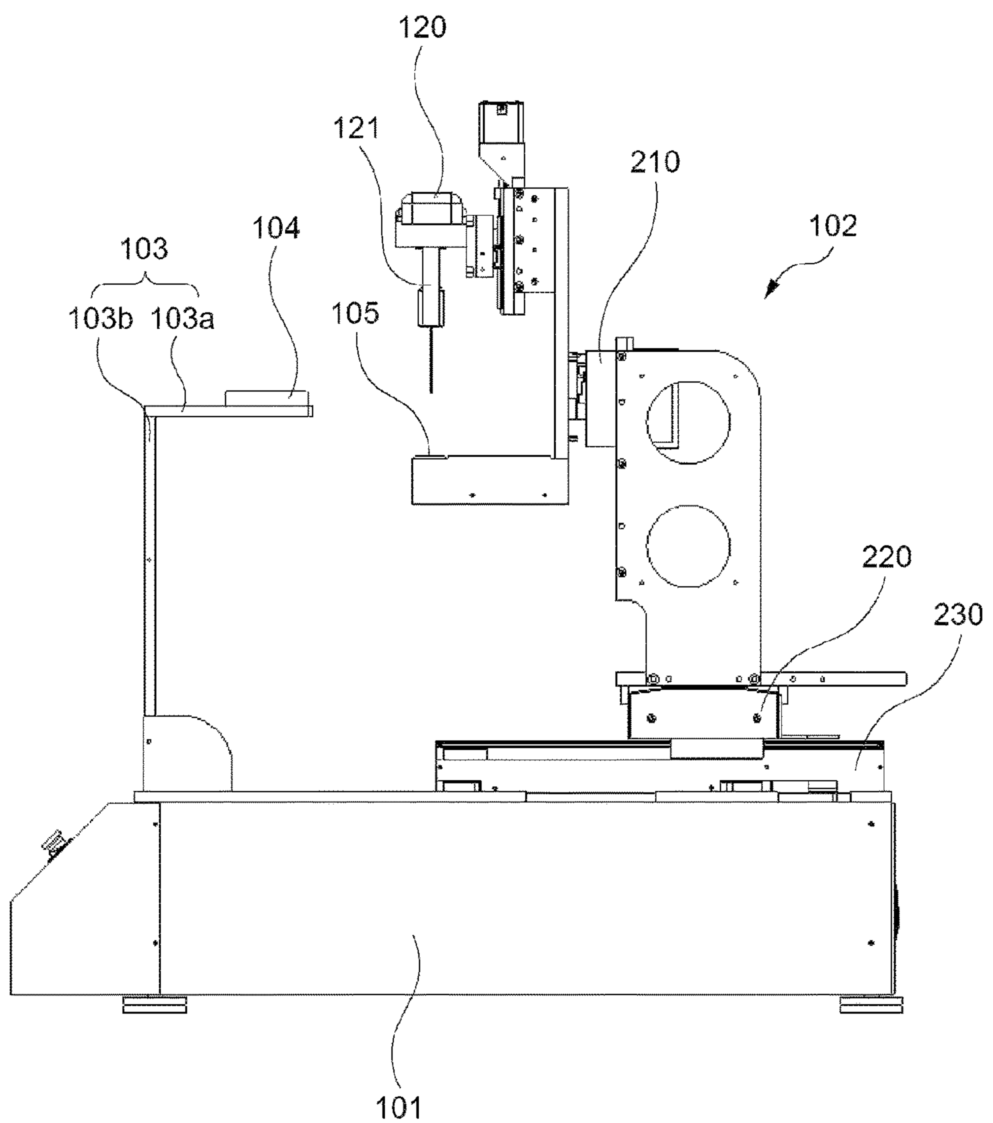
FIGS. 4A and 4B illustrate operations of a drive unit related to Y-axis directional movement of a frame according to one implementation of the present disclosure.
Figure 4B:
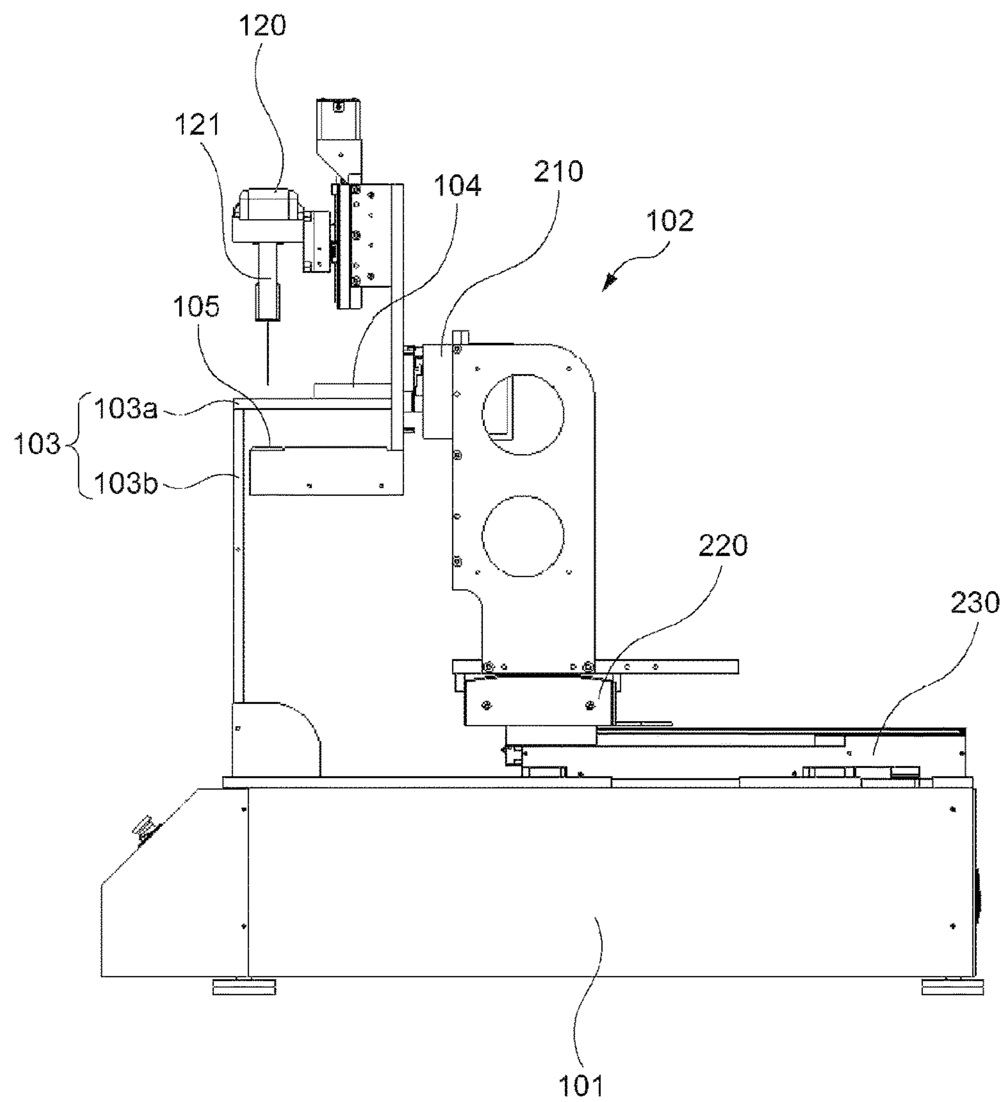

Referring to FIG. 4, the moving stroke of the third drive unit 230 may be about 310 mm. The distance between two limit sensors (i.e., one pair of limit sensors) located at both sides of the LM guide may be about 300 mm. In addition, a ball screw lead may have the size of about 2 mm. Meanwhile, the above-mentioned numerical values are merely examples, without being limited thereto.

The fourth drive unit 240 may move the camera 100 in the Z-axis direction. The fourth drive unit 240 may change a relative position of the camera 100 connected to the frame 102. If the camera 100 moves in the Z-axis direction as described above, the distance between the lens and the test table may be changed.

Figure 5A:
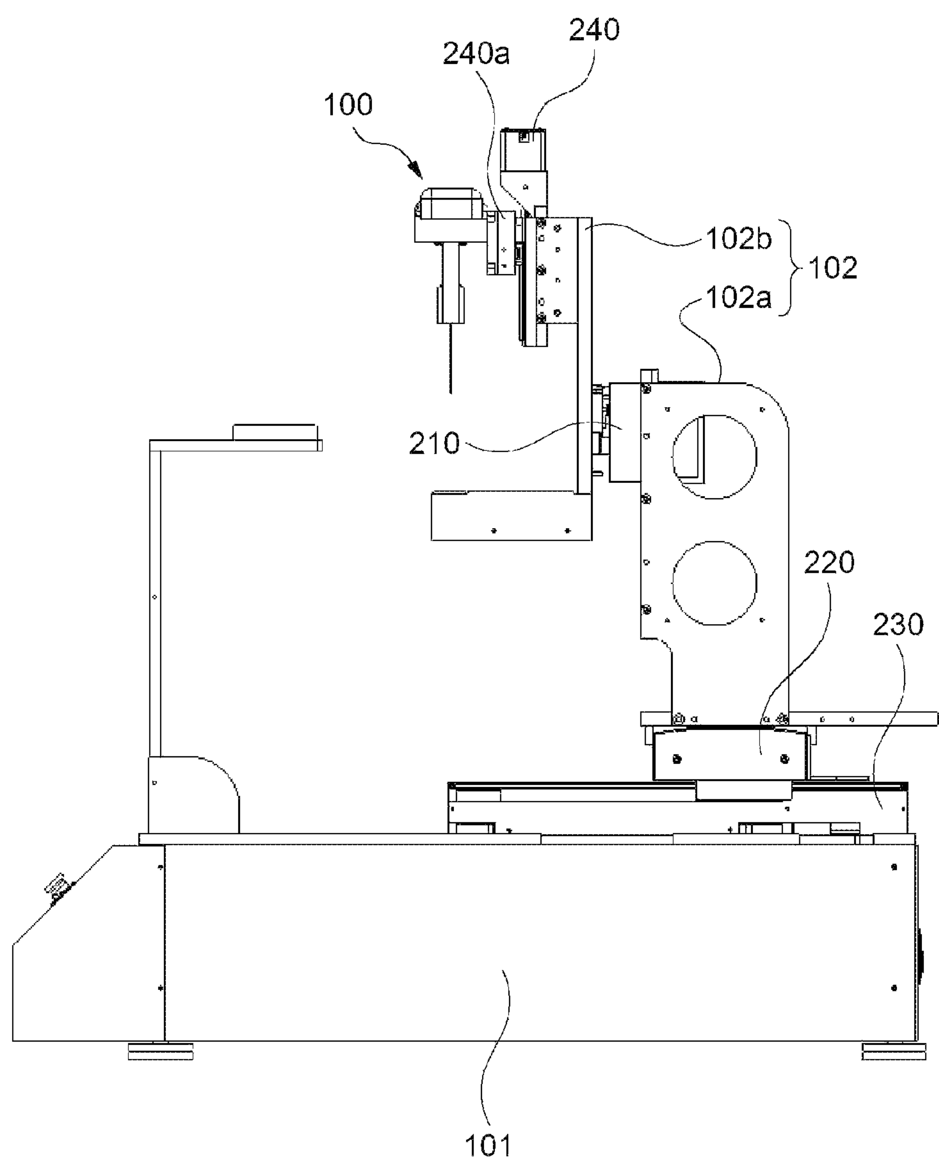
FIGS. 5A and 5B illustrate operations of a drive unit related to Z-axis directional movement of a camera according to one implementation of the present disclosure.
Figure 5B:
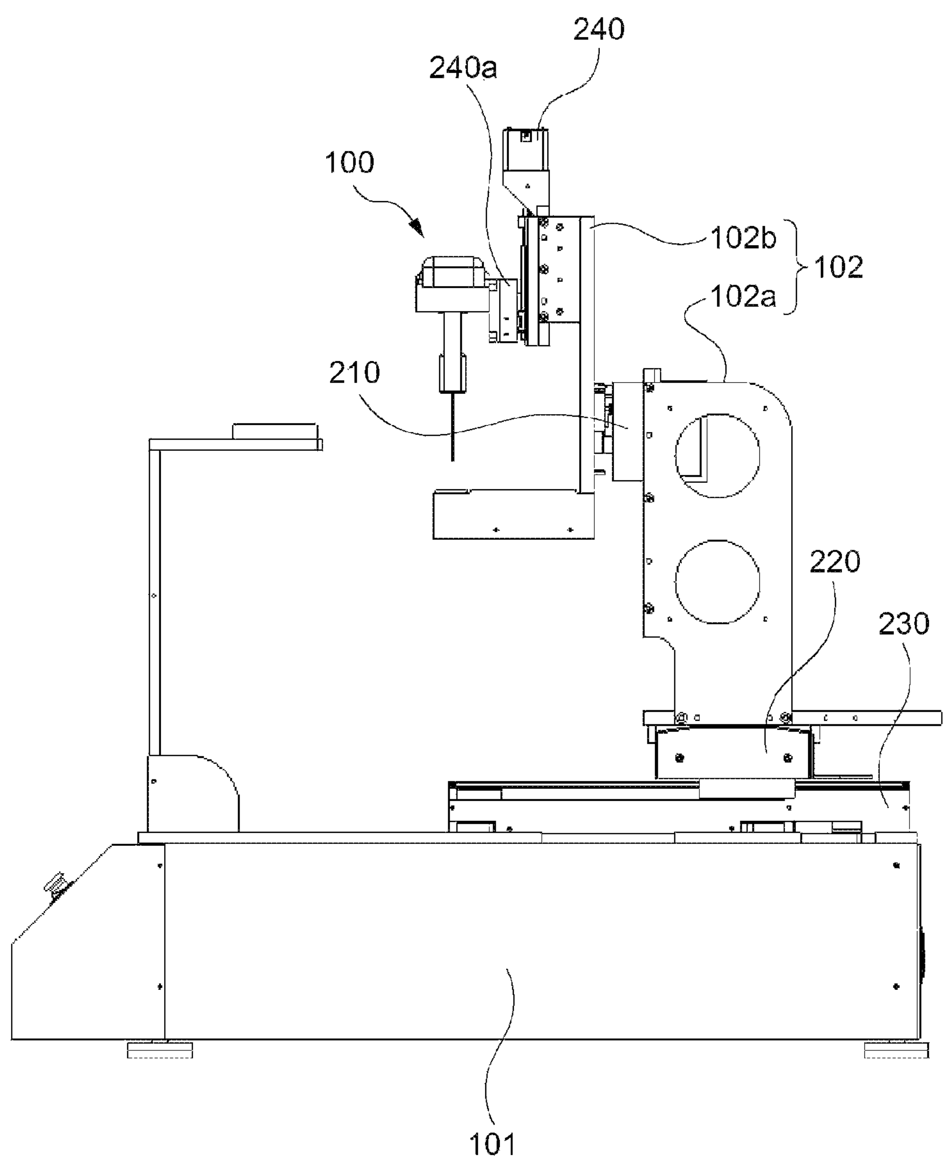

Referring to FIGS. 5A and 5B, a connection portion 240*a* for connecting the fourth drive unit 240 and the camera 100 may be arranged between the fourth drive unit 240 and the camera 100. In this case, the camera 100 may be fixed to the connection portion 240*a*, and the connection portion 240*a* may be movable in the Z-axis direction on the above frame 102.

In the meantime, detailed constituent elements of the fourth drive unit 240 may be identical to those of the first and second drive units 210 and 220.

Referring to FIGS. 5A and 5B, the moving stroke of the fourth drive unit 240 may be about 60 mm. The distance between two limit sensors (one pair of limit sensors) located at both sides of the LM guide may be about 50 mm. In addition, the ball screw lead may have the size of about 1 mm. Meanwhile, the above-mentioned numerical values are merely examples, and the present disclosure is not limited thereto.

Until now, the operations of the first to fourth drive units 210, 220, 230, and 240 and detailed constituent elements thereof have been disclosed above. A method for controlling the controller 300 to observe a plurality of fine objects will hereinafter be given.

Figure 6A:
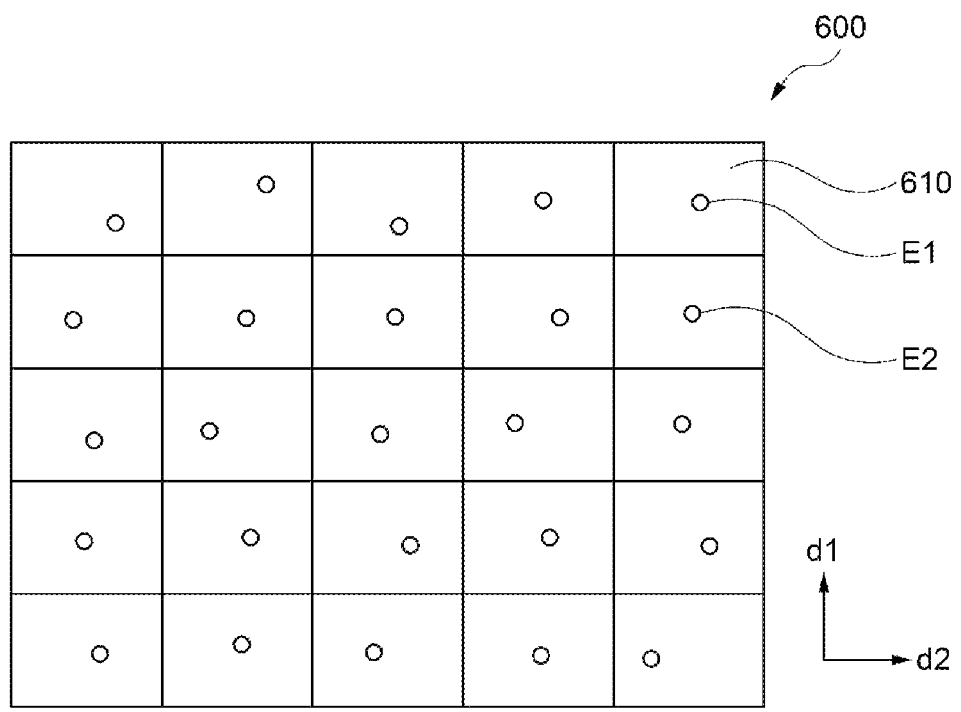
FIGS. 6A, 6B and 6C are conceptual diagrams illustrating an exemplary control method related to camera scanning according to one implementation of the present disclosure.

Referring to FIG. 6A, the plate 600 according to the present disclosure may include a plurality of partitioned wells 610. The respective wells 610 may contain fine objects E1 and E2 having different conditions. The fine objects having different conditions may refer to fine objects mixed with different materials.

In this case, the fine objects may be or include fish eggs, and the different material may be different harmful substances. In this case, harmfulness of respective harmful substances affecting fish eggs can be tested and measured.

The drive unit 200 may move the camera in one direction parallel to one surface of the plate 600 in such a manner that images of the above-mentioned fine objects can be respectively acquired.

In more detail, the drive unit 200 may move the first and second lenses 111 and 121 in at least one of first and second directions (d1, d2) and a third direction denoted by a combination of the first and second directions (d1, d2). In this case, the first and second directions (d1, d2) may respectively denote one direction parallel to the X-axis and the other direction parallel to the Y-axis. The third direction may denote a diagonal direction.

Here, the controller may perform control related to movement of the first and second directions of the first and second lenses 111 and 121 on the basis of the number of plural wells 610 of the plate 600, the size and position information of the wells 610.

Figure 6B:
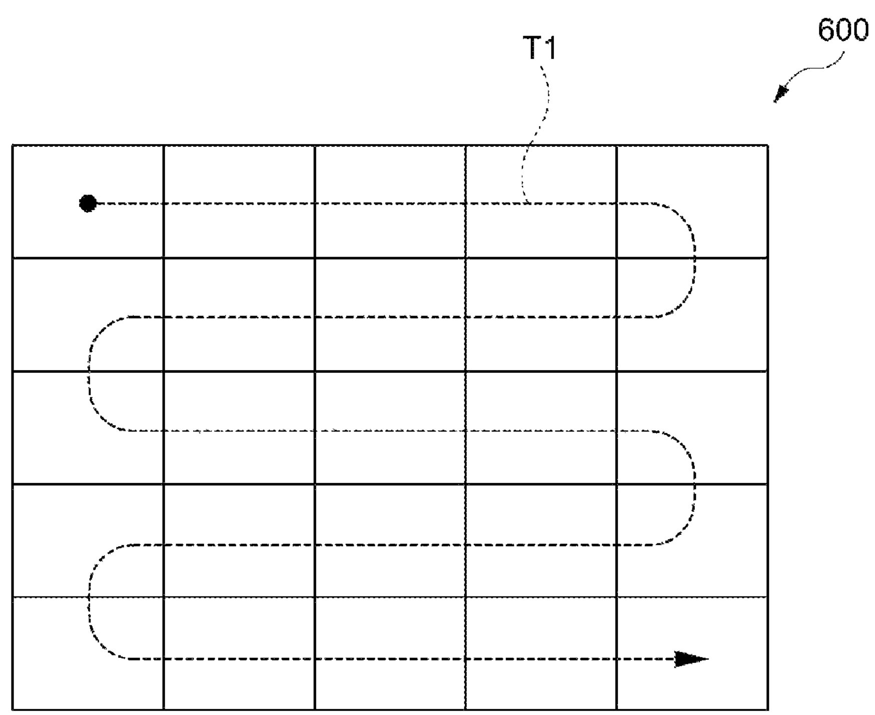

For example, as shown in FIG. 6B, the controller 600 may control the drive unit 200 to scan all or some of the wells 610 along a predetermined route T1.

Alternatively, the controller may perform control related to movement of the first and second directions of the first and second lenses 111 and 121 on the basis of a value of a user-input signal.

For example, the apparatus 1 for observing a fine object according to the present disclosure may include a user input unit. The user input unit may operate in an electronic or mechanical manner. For example, the user input unit may be a joystick. The controller may receive the signal value through the joystick, and may perform control related to movement of the first and second lenses 111 and 121 on the basis of the above-mentioned signal value.

Alternatively, the user may designate wells needed for image capture through the user input unit. In this case, the controller may establish the shortest route on the basis of positions of the designated wells. Furthermore, the controller may control the drive unit to move the first and second lenses 111 and 121 on the basis of the shortest route. Therefore, the first and second lenses 111 and 121 may move along the above-mentioned shortest route through a combination of X-axis movement and Y-axis movement.

Figure 6C:
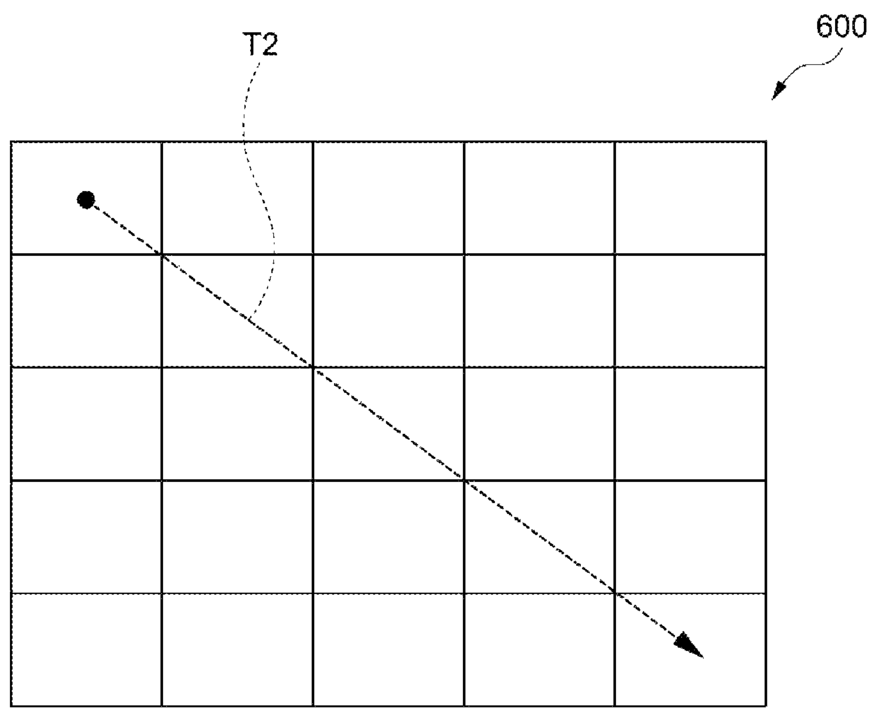

For example, as shown in FIG. 6C, the controller 600 may control the drive unit 200 in a manner that the first and second lenses 111 and 121 can scan a well selected from among the plurality of wells along a predetermined route T2.

Meanwhile, the embodiment of the present disclosure includes a plurality of observation objects and the observation time (e.g., the differentiation time of eggs) needed to observe objects is limited, such that there is a need to more efficiently perform image capture.

In accordance with one embodiment of the present disclosure, the controller may establish the shortest movement route on the basis of the position of at least some wells each having the above-mentioned fine object. In this case, the controller may determine the position of at least some wells each having the fine object on the basis of a predetermined method.

A detailed description of the predetermined method is as follows. The controller may determine the position of each well including the fine object on the basis of the position at which an image satisfying a predetermined condition is detected in a specific image acquired when the entirety of plural wells is captured at one time. Here, the predetermined condition may denote specific information as to whether the above image includes features of the shape or color of the prestored fine object.

Alternatively, although not shown in the drawings, each well of the plate may include a sensing unit configured to detect the fine object. In this case, the controller may determine the position of at least some wells (each having a fine object) from among the plurality of wells by determining whether each sensing unit of each well detects the fine object.

Meanwhile, wells having fine objects may be continuously or discontinuously arranged. For example, as shown in FIG. 7A, wells having fine objects may be spaced apart from each other.

Figure 7A:
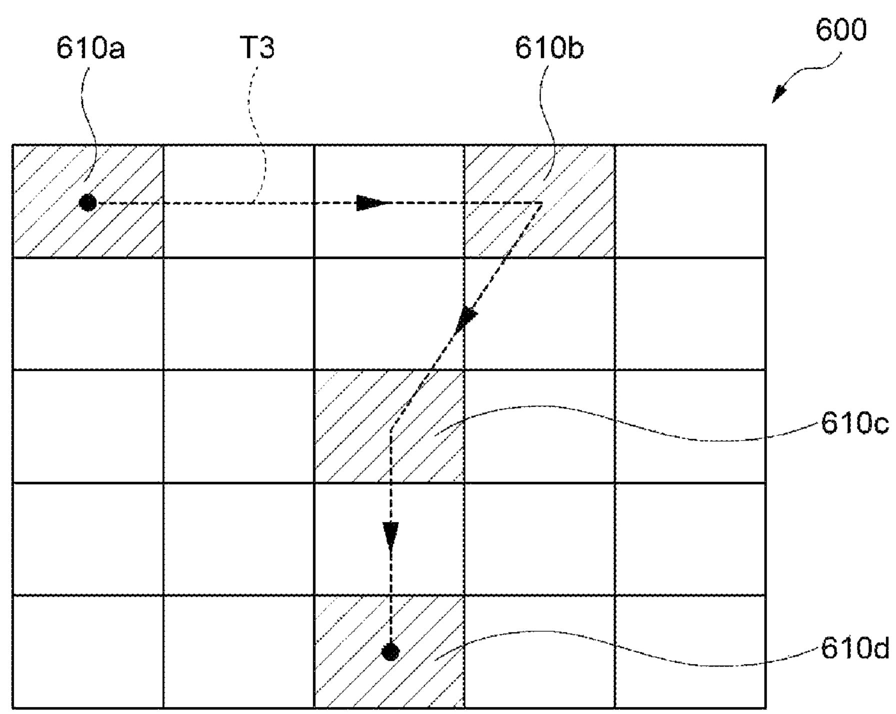
FIGS. 7A and 7B are conceptual diagrams illustrating a n exemplary control method for establishing the shortest movement route according to one implementation of the present disclosure.

For example, as shown in FIG. 7A, the controller may determine the position of some wells (610*a*, 610*b*, 610*c*, 610*d*) having fine objects from among the plurality of wells according to the predetermined method. The controller may establish the shortest movement route on the basis of the position of the above some wells (610*a*, 610*b*, 610*c*, 610*d*). For example, if any one 610*a* of the above some wells is designated as a start point, it may be possible to create six movement routes needed for six cases {(610*a*, 610*b*, 610*c*, 610*d*), (610*a*, 610*b*, 610*d*, 610*c*), (610*a*, 610*c*, 610*b*, 610*d*), (610*a*, 610*c*, 610*d*, 610*b*), (610*a*, 610*d*, 610*b*, 610*c*), and (610*a*, 610*d*, 610*c*, 610*b*)}. In this case, the controller may determine one route having the shortest movement route from among the six movement routes to be the shortest route. That is, according to the embodiment of the present disclosure, the movement route T3 denoted by (610*a*, 610*b*, 610*c*, 610*d*) may be determined to be the shortest movement route.

If the shortest movement route is decided, the controller may control the camera to move along the decided shortest movement route, and at the same time may control the drive unit to scan the plate using the camera.

Figure 7B:
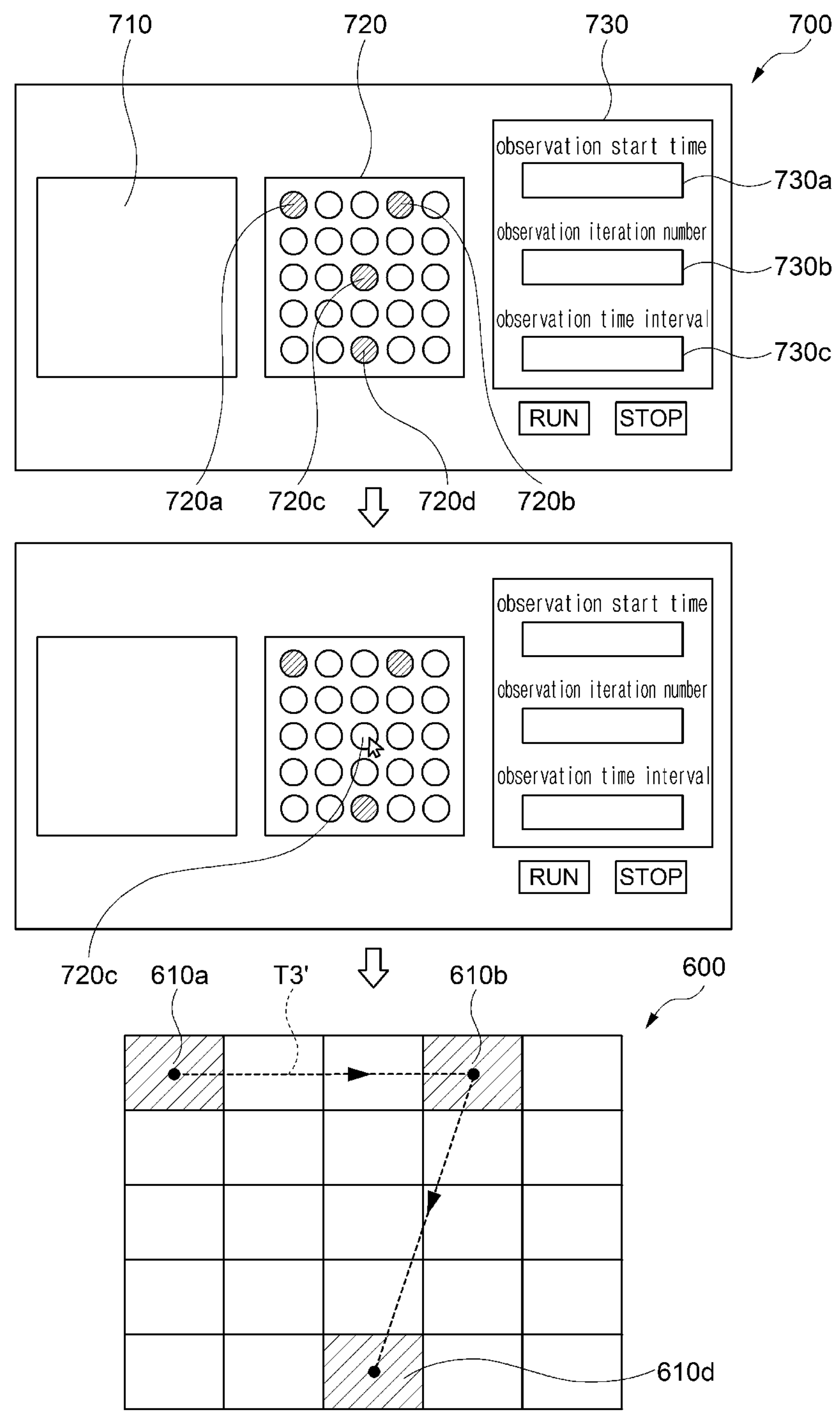

Referring to FIG. 7B, the apparatus for observing a fine object according to one embodiment of the present disclosure may further include a display unit 700 configured to output images captured by the camera. That is, the display unit 700 may convert the camera-captured image 710 into still images or moving images, and may display the still images or moving images in real time, such that the user can immediately recognize a current fine object being scanned.

Meanwhile, a plurality of images 720 respectively corresponding to wells may be output and displayed. Referring to FIGS. 7A and 7B, if the multiwell plate 600 includes N wells, N images respectively correspond to N wells may be output and displayed on the display unit 700. Furthermore, arrangement of the plurality of images may be achieved according to arrangement of the plurality of wells. For example, if the plurality of wells having an (N1×N2) matrix shape is arranged on the plate, the plurality of images may also be output and displayed in the form of an (N1×N2) matrix.

In addition, images 720*a*, 720*b*, 720*c*, and 720*d* corresponding to wells having fine objects from among the plurality of images displayed on the display unit 700 may be displayed in a different way from the remaining images. Therefore, the user can recognize the position of wells to be immediately scanned.

Furthermore, the controller may change the shortest movement route on the basis of the position of wells corresponding to user-selected images from among the plurality of images.

Referring to FIGS. 7B(*a*) and 7B(*b*), selection completion of images corresponding to wells having fine objects may be visually displayed. If the user releases selection of at least some images 720*c* from among the above images using the input device, wells corresponding to the selection-released images 720*c* may be excluded from the movement route. Referring to FIG. 7B(C), the controller may finally re-determine the shortest movement route on the basis of the position of wells corresponding to user-selected images (see T3' of FIG. 7B(*c*)).

Although FIG. 7B illustrates an example in which wells having fine objects are decided by the controller and some of the wells are excluded from the movement route through user input for convenience of description and better understanding of the present disclosure, the scope or spirit of the present disclosure is not limited thereto.

For example, after wells having fine objects are decided, if the user additionally selects images corresponding to the remaining wells other than the decided wells, the controller may re-establish the shortest movement route by adding wells other than the decided wells.

In accordance with one embodiment of the present disclosure, the controller may control the drive unit in such a manner that the camera performs first movement in which the camera moves along the shortest route at one side of the plate and then performs second movement in which the camera moves along the shortest route at the other side of the plate.

In this case, one side and the other side of the plate may respectively denote an upper part and a lower part of the fine objects. That is, the camera arranged at an upper side of the fine objects performs first movement while moving in a plane direction of the plate as shown in FIG. 2A. Then, the camera arranged at a lower side of the fine objects performs second movement while moving in a plane direction of the plate as shown in FIG. 2B.

As described above, prior to execution of the second movement after completion of the first movement, the camera may be rotated by the drive unit by about 180° with respect to fine objects.

Furthermore, the controller may control the drive unit in such a manner that the camera repeatedly performs one set of the first movement and the second movement according to a user-selected value indicating the number of iterations entered by the user.

Referring to FIG. 7B, the user input unit 730 may be displayed on the display unit 700. The user may input a specific value corresponding to the number of iterations through the user input unit 730*b*. For example, if the number of iterations is set to '2' by the user, the camera may sequentially perform first movement, perform second movement, and then sequentially perform the first movement and the second movement. The camera may rotate in the range from the first movement to the second movement as described above.

In addition, the controller may control the drive unit in such a manner that the camera performs one set of the above-mentioned movements and then performs the next set of such movements at intervals of a predetermined time corresponding to a user-selected time interval.

Referring to FIG. 7B, the user may input the time interval value through the user input unit 730*c* displayed on the display unit 700.

For example, if the number of iterations is set to '2' and the time interval value is set to '1' indicating one minute, the camera finishes one set of the first movement and the second movement and then performs the next set of the first movement and the second movement after lapse of 1 minute.

Referring to FIG. 7B, the user may input an observation start time through the user input unit 730*a* displayed on the display unit 700. If a current time reaches the observation start time, the controller may control the drive unit to start camera scanning.

A method for observing a fine object contained in one well will hereinafter be described.

For convenience of description and better understanding of the present disclosure, the term 'first image' may refer to an image (still image or moving image) acquired when the fine object is captured by the first lens at a first magnification, and the term 'second image' may refer to an image (still image or moving image) acquired when the fine object is captured by the second lens at a second magnification. Here, the second magnification may be higher than the first magnification.

Figure 8:
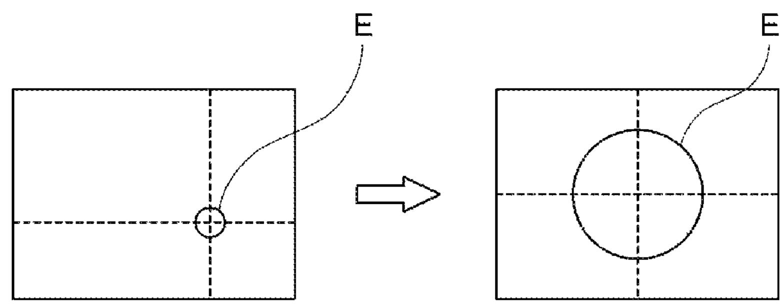
FIG. 8 is a conceptual diagram illustrating an exemplary image acquisition control method for use in the apparatus for observing a fine object according to one implementation of the present disclosure.

Referring to FIG. 8, the controller may determine a detailed position of the fine object on the basis of the first image, and may control the camera to capture the second image including a fine-object image higher in magnification than the first image on the basis of the determined detailed position of the fine object. Here, the left drawing of FIG. 8 may refer to the first image, and the right drawing of FIG. 8 may refer to the second image.

In more detail, the controller may determine a specific part that satisfies a predetermined condition in the fine-object image magnified at the first magnification through the first lens 111, to be the detailed position of the fine object.

In more detail, the controller may test the fine-object image magnified at the first magnification on a pixel basis according to a predetermined color, shape, etc., and may thus determine the detailed position of the fine object.

In addition, the controller may also determine the detailed position of the fine object according to an automatic edge detection algorithm or an outlier removal method.

Meanwhile, the fine-object image magnified at the first magnification may be displayed in real time through the display unit. In this case, a target object may be measured through an image program measurement device, and a center point, a maximum distance, an average distance, a minimum distance, etc. of the target object may also be measured in the form of dot, line, circle, arc, polygon, polyline, oval, and the like through the image program measurement device.

If the object is captured at the second magnification, the controller may adjust the position of the camera on the basis of the detailed position of the fine object. In more detail, adjusting the camera position may refer to replacement between the position of the first lens and the position of the second lens. By camera position adjustment, the fine-object image magnified at the second magnification may be located at the center of the second image. Furthermore, the controller may acquire the position and size information of the fine object on the basis of the fine-object image magnified at the first magnification and the fine-object image magnified at the second magnification. Through a series of the above-mentioned processes, the position and size position of the fine objects contained in the respective wells may be acquired.

In addition, through movement of the first and second lenses 111 and 121, the position and size information of plural fine objects contained in plural wells may also be acquired.

Images of the fine objects of the respective wells of the captured plate 104 may be synthesized into one image (still image or moving image), and the resultant synthesized image may then be provided.

In addition, the controller may control the camera 100 to capture the objects on the basis of a predetermined start time, a predetermined end time, and a capturing period. That is, the camera 100 may automatically capture an image (still image or moving image) at intervals of a predetermined capturing period ranging from the start time to the end time.

As described above, the fine objects may be fish eggs. The controller may determine movement of the camera or the capture time of the camera on the basis of the differentiation time of the fish eggs.

For example, at least one of the camera movement speed and the capture time of each well may be determined on the basis of the differentiation time of fish eggs and the decided shortest movement route in such a manner that scanning can be completed within the differentiation time of fish eggs.

Alternatively, as described above, if the number of iterations is input by the user, at least one of the camera movement speed and the capture time of each well may be determined on the basis of the differentiation time of fish eggs, the determined shortest movement route, and the user-input iteration number in such a manner that the camera movement that is repeated according to the iteration number entered by the user within the differentiation time of fish eggs.

Alternatively, if the user inputs the number of iterations (i.e., the iteration number) and the time interval value as described above, at least one of the camera movement speed and the capture time of each well may be determined on the basis of the determined shortest movement route, the user-input iteration number, and the user-input time interval.

Meanwhile, different fish types may have different differentiation times of fish eggs. Here, the differentiation times for respective fish types may also be well known to those skilled in the art as necessary.

For example, the camera capturing may be started under the condition that plural fish eggs are contained in the respective wells as shown in FIG. 6A. As shown in FIG. 6B, if the predetermined scanning route is set to T1 as shown in FIG. 6B, the scanning speed (a drive control speed of the drive unit) or a time consumed in each well may be adjusted in such a manner that scanning can be completed within the differentiation time of fish eggs. In each well, low-magnification capturing and high-magnification capturing may be sequentially carried out as shown in FIG. 8.

That is, according to the present disclosure, in each well, the camera position may be controlled by the fourth drive unit, and the second and third drive units may control the camera position in association with movement among wells. Meanwhile, after scanning of the upper part of the plate is completed, the camera may move in a downward direction by the first drive, and scanning of the lower part of the plate may be started by the first drive.

That is, the controller according to the present disclosure automatically controls a scanning route according to unique attribute information of the plate, and a consumption time caused by the manual operation associated with conventional camera movement between wells of the related art may be greatly reduced.

In the meantime, the controller may control the camera 100 to scan the entirety of wells of the plate 104 or to selectively scan some of the wells of the plate 104.

In addition, the apparatus for observing a fine object according to the present disclosure may include a backlight unit 105 that is located to face the camera 100 and emits light to the fine object. The camera 100 and the backlight unit 105 may be incorporated into the frame 102.

In this case, the fine object receives light through the backlight unit 105, such that the observation apparatus can acquire a higher-definition image for the fine object.

The mobile terminal according to the foregoing embodiments is not restricted to the configuration and method of the embodiments set forth herein. Therefore, some or all of the above-described embodiments may be selectively combined to make various modifications.

As is apparent from the above description, the apparatus for observing a fine object according to an embodiment of the present disclosure can capture images of only wells each having one or more fine objects by allowing a camera to move along the shortest movement path, such that the observation apparatus can more rapidly capture images of a plurality of fine objects. In this case, the camera may be movable not only in first and second directions (x and y directions) corresponding to a horizontal direction, but also in a third direction corresponding to a diagonal direction composed of a combination of the first and second directions, such that the shortest movement route can be established. Therefore, if the fine objects are fish eggs, the observation apparatus can capture and image a plurality of eggs within a restricted differentiation time of fish eggs.

The observation apparatus according to the present disclosure can capture and image an upper or lower part of fine objects because a camera rotates about the fine objects. Therefore, the observation apparatus can acquire higher-quality images (still images or moving images) even when fine objects have sunk to the bottoms of wells of a plate.

The observation apparatus according to the present disclosure can acquire higher-definition images because fine objects receive light from a backlight unit.

The observation apparatus according to the present disclosure can measure the heart rate of a plurality of fine objects contained in respective wells according to a predetermined method based on images (still images or moving images) captured by a camera.

Only a few implementations and examples are described and other implementations, enhancements and variations can be made based on what is described and illustrated in this patent document.

What is claimed is:

1. An apparatus for observing a fine object comprising:

a camera configured to capture each of a plurality of fine objects contained in at least some of partitioned wells of a plate;

a drive unit coupled to the camera and configured to allow the camera to relatively move with respect to the plate in such a manner that the camera scans the plate; and a controller coupled to the drive unit and configured to control the drive unit in such a manner that the camera captures the at least some of partitioned wells having fine objects, wherein the controller operates to determine a shortest movement route of the camera based on a position of the at least some of partitioned wells having the fine objects, and control the drive unit to move the camera in the determined shortest movement route, and when the camera captures each of the at least some of the partitioned wells having the plurality of fine objects, the camera captures each well at a first magnification and additionally captures each well at a second magnification higher than the first magnification.

2. The apparatus according to claim 1, wherein the controller determines the positions of the at least some of the partitioned wells having the fine objects according to a predetermined method.

3. The apparatus according to claim 1, wherein the controller operates to determine the positions of the at least one of the partitioned wells based on an image capturing all of the partitioned wells and having a specific position satisfying a predetermined condition.

4. The apparatus according to claim 1, further comprising:

a display unit configured to output an image captured by the camera, wherein the image includes a still image and a moving image.

5. The apparatus according to claim 4, wherein the display unit operates to output a plurality of images corresponding to the respective wells, and the controller changes the shortest movement route on the basis of the positions of wells corresponding to user-selected images among the plurality of images.

6. The apparatus according to claim 1, wherein the controller controls the drive unit in a manner that the camera sequentially performs first movement and second movement, wherein the first movement causes the camera to move along the shortest movement route at one side of the plate, and the second movement causes the camera to move along the shortest movement route at the other side of the plate.

7. The apparatus according to claim 6, wherein the camera is located at one side and the other side of the plate and operates to rotate about the fine object by the drive unit in such a manner that the camera captures an upper part of the fine object and a lower part of the fine object.

8. The apparatus according to claim 1, wherein:

the controller determines a detailed position of the fine object as a specific part of an image captured at the first magnification, the image satisfying a predetermined condition; and when the camera additionally captures each well at the second magnification, the controller controls the drive unit in a manner that the position of the camera is adjusted on the basis of the determined detailed position of the fine object.

9. The apparatus according to claim 8, wherein:

a fine-object image magnified at the second magnification is located at the center of the captured image.

10. The apparatus according to claim 9, wherein the drive unit controls the camera to move in a single direction parallel to one surface of the plate having the fine object.

11. The apparatus according to claim 10, wherein the single direction is at least one of first and second directions orthogonal to each other and a third direction denoted by a combination of the first direction and the second direction.

12. The apparatus according to claim 1, further comprising:

a backlight unit located to face the camera, and configured to emit light to the fine object.

13. The apparatus according to claim 12, wherein the camera and the backlight unit are integrated into a frame in such a manner that the camera rotates along with the backlight unit.

14. An apparatus for observing a fine object comprising:

a camera configured to capture each of a plurality of fine objects contained in at least some of partitioned wells of a plate;

a drive unit coupled to the camera and configured to allow the camera to relatively move with respect to the plate in such a manner that the camera scans the plate; and a controller coupled to the drive unit and configured to control the drive unit in such a manner that the camera captures the at least some of partitioned wells having fine objects, wherein the controller operates to determine a shortest movement route of the camera based on a position of the at least some of partitioned wells having the fine objects, and control the drive unit to move the camera in the determined shortest movement route, wherein the camera is located at one side and the other side of the plate and operates to rotate about the fine object by the drive unit in such a manner that the camera captures an upper part of the fine object and a lower part of the fine object, and wherein the controller controls the drive unit in such a manner that the camera repeatedly performs a single set of the first movement and the second movement according to the number of iterations entered by a user.

15. The apparatus according to claim 14, wherein the controller controls the drive unit in such a manner that the camera performs the single set of movements and then performs a next set of movements according to a time interval value entered by the user.

16. The apparatus according to claim 14, wherein:

if the fine object includes a fish egg, at least one of a movement speed of the camera and an image capture time for each well is determined on the basis of a differentiation time of the fish egg, the determined shortest movement route, and the number of iterations entered by the user in such a manner that camera movement is repeatedly performed according to the user-input iteration number received within the differentiation time of the fish egg.

17. The apparatus according to claim 15, wherein:

if the fine object includes a fish egg, at least one of a movement speed of the camera and an image capture time for each well is determined on the basis of a differentiation time of the fish egg, the determined shortest movement route, and the number of iterations entered by the user in such a manner that camera movement is repeatedly performed according to the user-input iteration number received within the differentiation time of the fish egg.

18. An apparatus for observing a fine object comprising:

a camera configured to capture each of a plurality of fine objects contained in at least some of partitioned wells of a plate;

a drive unit coupled to the camera and configured to allow the camera to relatively move with respect to the plate in such a manner that the camera scans the plate; and a controller coupled to the drive unit and configured to control the drive unit in such a manner that the camera captures the at least some of partitioned wells having fine objects, wherein the controller operates to determine a shortest movement route of the camera based on a position of the at least some of partitioned wells having the fine objects, and control the drive unit to move the camera in the determined shortest movement route, and wherein if the fine object includes a fish egg, at least one of a movement speed of the camera and an image capture time for each well is determined on the basis of a differentiation time of the fish egg and the determined shortest movement route in such a manner that the scanning is completed within the differentiation time of the fish egg.

* * * * *